United States Patent [19]
Dabney

[11] Patent Number: 6,059,717
[45] Date of Patent: May 9, 2000

[54] SEXUAL AID

[76] Inventor: J. Conway Dabney, 2125 Wren Way, Clearwater, Fla. 34624

[21] Appl. No.: 09/128,213

[22] Filed: Aug. 3, 1998

Related U.S. Application Data

[63] Continuation-in-part of application No. 08/574,208, Dec. 18, 1995, Pat. No. 5,787,892.
[51] Int. Cl.⁷ ...................................................... A61F 5/00
[52] U.S. Cl. .............................................................. 600/38
[58] Field of Search .................................... 128/842, 844, 128/918; 600/38, 39

[56] References Cited

U.S. PATENT DOCUMENTS

| | | | |
|---|---|---|---|
| 3,910,262 | 10/1975 | Stoughton | 600/38 |
| 3,926,178 | 12/1975 | Feldzamen | 600/38 |
| 5,823,939 | 10/1998 | Tsagarakis | 600/38 |

*Primary Examiner*—Michael A. Brown

[57] ABSTRACT

A sexual aid comprising a cylindrical central first section having a circular cross-section along its entire length. A distal section formed in a generally cone-shaped configuration with an axis coextensive with the axis of the central first section provides a generally planar radial first abutment surface between the central section and the distal section. A proximal section is provided for use as a handle. The proximal section has an axis coextensive with the axis of the central first section and the distal section. A second abutment surface is provided adjacent to the proximal end of the central first section.

7 Claims, 5 Drawing Sheets

SEXUAL AID

RELATED APPLICATION

This application is a continuation in part of application Ser. No. 08/574,208 filed Dec. 18, 1995, now U.S. Pat. No. 5,787,892.

BACKGROUND OF THE INVENTION

1. Field of the Invention

The present invention relates to a sexual aid and, more particularly, pertains to providing abutment surfaces positionable on opposite sides of an anal sphincter to ensure proper positioning and retention of a sexual aid.

2. Description of the Prior Art

The use of sexual aids of known designs and configurations is known in the prior art. More specifically, sexual aids of known designs and configurations heretofore devised and utilized for the purpose of utilizing sexual aids through a wide variety of methods and apparatuses are known to consist basically of familiar, expected and obvious structural configurations, notwithstanding the myriad of designs encompassed by the crowded prior art which have been developed for the fulfillment of countless objectives and requirements.

By way of example, the prior art discloses in U.S. Pat. No. 4,216,783 to Kaiser et al., discloses a pneumatic monitor for indicating strength of contractile muscles.

U.S. Pat. No. 3,926,178 to Feldzamen discloses an apparatus for aiding the voluntary exercising of sphincter muscles.

U.S. Pat. No. 5,433,216 to Sugrue et al., discloses an intra-abdominal pressure measurement apparatus and method.

U.S. Pat. No. 5,005,586 to Lahr discloses a method for exercising a patients anal canal.

U.S. Pat. No. 3,625,199 to Summers discloses an implantable pressure indicator.

Lastly, European Patent Number 50,983 discloses a patient anaesthesia depth monitoring system.

While these devices fulfill their respective, particular objectives and requirements, the aforementioned patents do not describe a sexual aid that provides abutment surfaces positionable on opposite sides of an anal sphincter to ensure proper positioning and retention of a sexual aid.

In this respect, the sexual aid according to the present invention substantially departs from the conventional concepts and designs of the prior art, and in so doing provides an apparatus primarily developed for the purpose of providing abutment surfaces positionable on opposite sides of an anal sphincter to ensure proper positioning and retention of a sexual aid.

Therefore, it can be appreciated that there exists a continuing need for new and improved sexual aid which can be used for providing abutment surfaces positionable on opposite sides of an anal sphincter to ensure proper positioning and retention of a sexual aid. In this regard, the present invention substantially fulfill this need.

SUMMARY OF THE INVENTION

In view of the foregoing disadvantages inherent in the known types of sexual aids of known designs and configurations now present in the prior art, the present invention provides an improved sexual aid. As such, the general purpose of the present invention, which will be described subsequently in greater detail, is to provide a new and improved sexual aid apparatus and method which has all the advantages of the prior art and none of the disadvantages.

To attain this, the present invention essentially comprises a new and improved sexual aid positionable in a user's anal sphincter for support therein by opposed radial abutment surfaces comprising, in combination, a cylindrical central first section, having a circular cross-section along its entire length. The central first section has an axial length of about between about 1 inch and 2½ inches, preferably about 1¾ inches and a diameter of between ½ inch and ⅞ inch, preferably ¾ inch. A distal section is formed in a generally cone-shaped configuration with an axis coextensive with the axis of the central first section. The distal section has a length of between about 1 inch and 2 inches, preferably about 1½ inches and has a maximum diameter adjacent to the distal end of the central section with a diameter of between about 1¼ inches and 1¾ inches, preferably 1½ inches to provide a generally planar radial first abutment surface between the central section and the distal section. A proximal section in a generally spherical configuration is provided for use as a handle. The proximal section has an axis coextensive with the axis of the central first section and the distal section with a maximum diameter of between about 1½ inches and 2 inches, preferably 1¾ inches. Next provided is a central toroidal section between the central first section and the proximal section. The central toroidal section has an axial length of between ¼ inch and ½ inch, preferably ⅜ inch and a maximum radial dimension of between about 1 inch and 1½ inches, preferably about 1¼ inches, providing an enlargement which is between about ½ inch in diameter greater than the cylinders on the opposite sides. A cylindrical second section is provided between the toroidal section and the proximal section. The cylindrical second section has an axial length of between about ½ inch and ¾ inch, preferably ½ inch, and a diameter of between about ½ and ⅞ inch, preferably ¾ inch. The toroidal section forms a second abutment surface between the central first section and the toroidal section. The entire device is formed of an elastomeric material with a lubricous surface and limited resilience.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sexual aid which has all the advantages of the prior art sexual aids of known designs and configurations and none of the disadvantages.

It is another object of the present invention to provide a new and improved sexual aid which may be easily and efficiently manufactured and marketed.

It is a further object of the present invention to provide a new and improved sexual aid which is of a durable and reliable construction.

An even further object of the present invention is to provide a new and improved sexual aid which is susceptible of a low cost of manufacture with regard to both materials and labor, and which accordingly is then susceptible of low prices of sale to the consuming public, thereby making such sexual aid economically available to the buying public.

Still yet another object of the present invention is to provide a new and improved sexual aid which provides in the apparatuses and methods of the prior art some of the advantages thereof, while simultaneously overcoming some of the disadvantages normally associated therewith.

Still another object of the present invention is to provide a sexual aid for providing abutment surfaces positionable on opposite sides of an anal sphincter to ensure proper positioning and retention of a sexual aid.

Lastly, it is an object of the present invention to provide a new and improved device for sexual aid comprising a cylindrical central first section having a circular cross-section along its entire length. A distal section is formed in a generally cone-shaped configuration with an axis coextensive with the axis of the central first section to thereby provide a generally planar radial first abutment surface between the central section and the distal section. A proximal section is provided for use as a handle. The proximal section has an axis coextensive with the axis of the central first section and the distal section. A second abutment surface is provided adjacent to the proximal end of the central first section.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
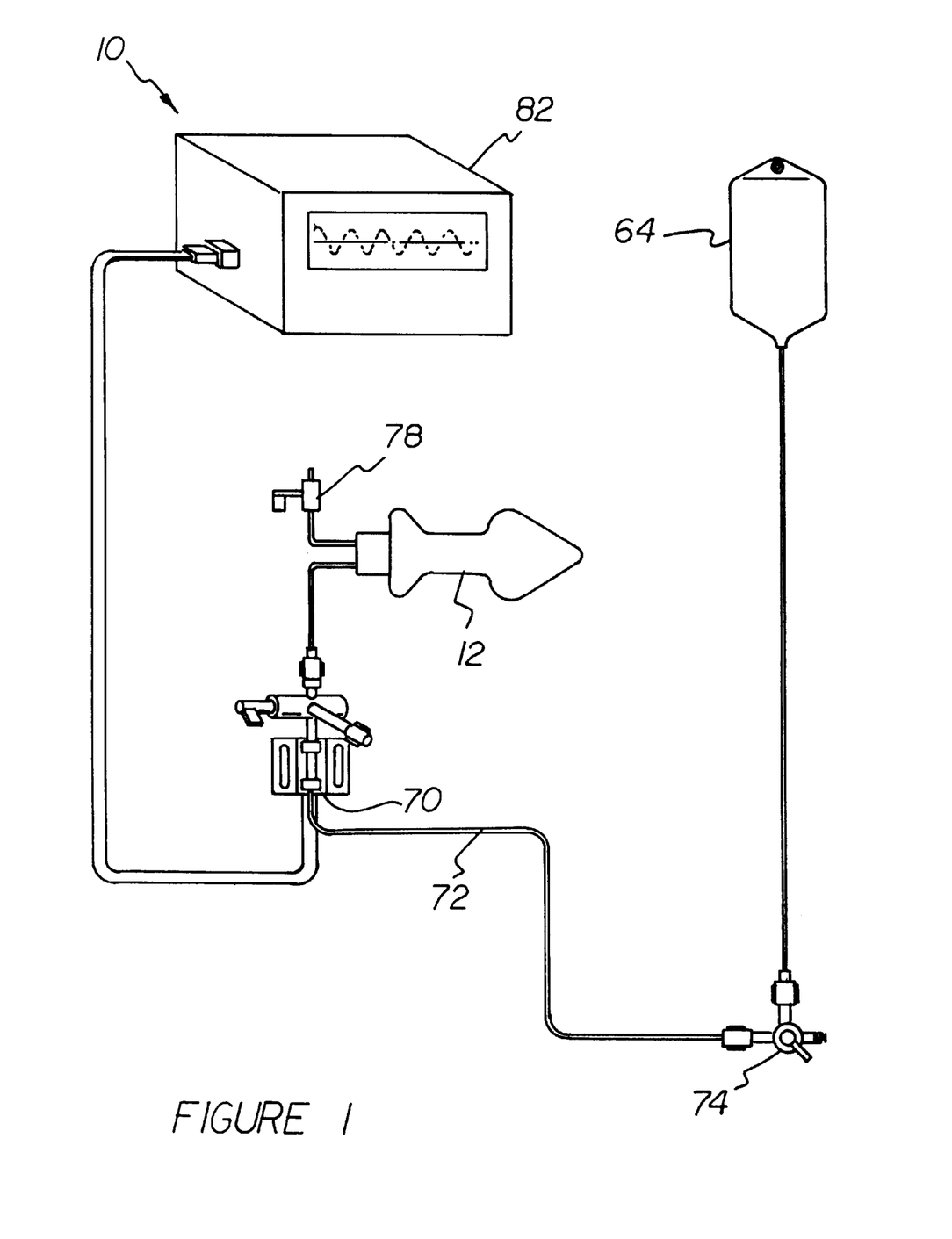
FIG. 1 is a perspective illustration of the preferred embodiment of the sexual aid constructed in accordance with the principles of the present invention.

With reference now to the drawings, and in particular to FIG. 1 thereof, a new and improved sexual aid embodying the principles and concepts of the present invention and generally designated by the reference numeral 10 will be described.

The present invention, the new and improved anal orgasm monitor, is comprised of a plurality of components. Such components in their broadest context include a core, windows, a head and a tail. Such components are individually configured and correlated with respect to each other so as to attain the desired objective.

Figure 2:
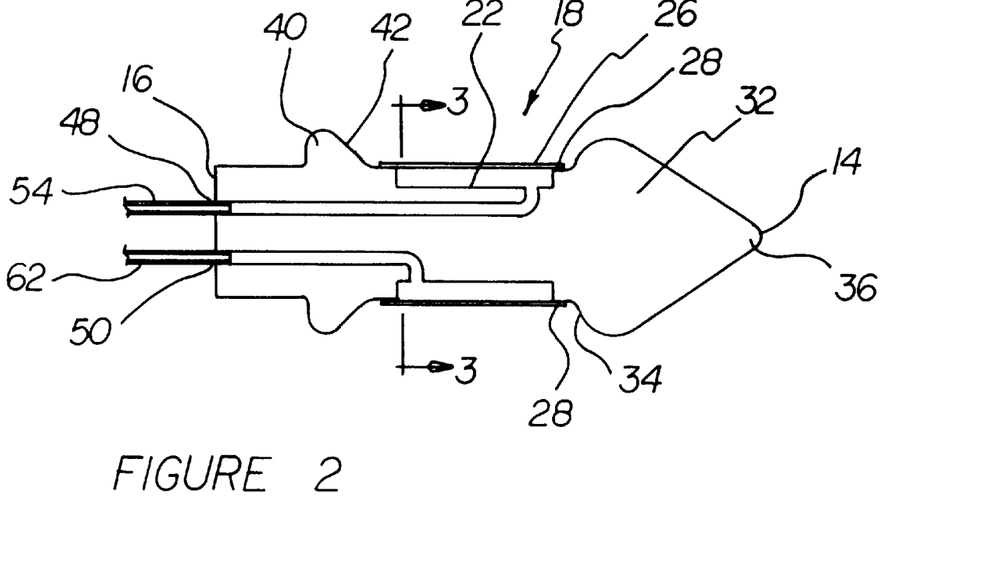
FIG. 2 is an enlarged cross-sectional view of the core shown in FIG. 1.
Figure 3:
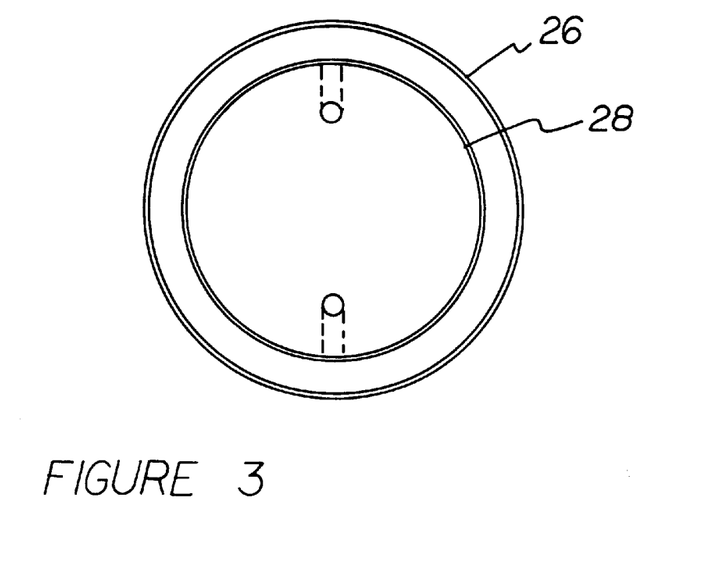
FIG. 3 is a cross-sectional view taken along line 3—3 of FIG. 2.

More specifically, the present invention may be considered as a system 10. The central component of such a system is a core 12. The core is formed of a generally cylindrical configuration. It is fabricated of a relatively rigid plastic material, preferably polyethylene terepthalate (PET). It has a distal end 14 and a proximal end 16. The core also has an axial length of about 4 inches. The core has a central section 18 of a reduced diameter of about ⅞ inch. The axial length of the central section is about 1½ inches.

The central section is formed with an annular recess 22. Such recess has a generally rectangular cross-sectional configuration.

Next provided is an annular sheet 26. The sheet material is preferably of a flexible, essentially inelastic material, preferably polyethylene. Such material is in a generally annular configuration over the central section of the core. It is located so as to overlie the recess. An adhesive 28 is used for securing the material to the core peripherally at its axial edges.

The plastic sheet material functions as a diaphragm for changing shape in response to applied pressure as through the anal sphincter muscle.

Next provided as a component of the system 10 is a head 32. The head is located adjacent to the distal end of the core. The proximal end 34 of the head is located adjacent to the distal end of the central section. The head has a diameter at its largest point, adjacent to the proximal end, of about 1½ inches. The distal end 36 of the head is of a reduced diameter to form a generally cone-shaped configuration. The design of the head is to facilitate insertion and, in combination with the tail, to maintain the proper position of the central section during operation and use.

Complimentary to the head is a tail 40. The tail functions as a barrier to preclude excess insertion of the core into the anal canal. The tail is located adjacent to the proximal end of the core. The distal end 42 of the tail is located at the proximal end of the central section. It has a diameter of about 1½ inches at its widest point. The proximal end of the tail and the distal end of the core are spaced by about 1½ inches.

Formed in the core is a first axial aperture 48 and a second axial aperture 50. The apertures extend through the proximal end of the core.

In association with the first aperture, there is provided an air outlet tube 54. Such tube has a proximal end remote from the core. It also has a distal end coupled to the core at the second axial aperture.

A water inlet tube 62 is then provided. Such water inlet tube has a proximal end remote from the core and it also has a distal end coupled to the first axial aperture.

Located remote from the core 12 and at an elevated location is a bag 64 for a supply of fluid, preferably water, for use in filling the core. The water from the bag enters the region of the recess beneath the sheet material through a line coupled to the water inlet tube while the air from the recess beneath the sheet material through a line coupled to the air outlet tube. Coupling of such lines to the recess are at axially spaced locations to facilitate the smooth flow of water and air during the filling process.

A transducer 70 is then coupled to the proximal end of the water inlet tube. It has an associated fill tube 72 and an inlet valve 74. This allows the selective adding of water to the inlet tube and core. The valve when closed also allows for sealing of water within the tube and core.

An outlet valve 78 is next provided at the proximal end of the air outlet tube. Such outlet tube valve allows the escape of air from the core and associated tubes during the filling of the core with water. The valve also functions to close off the air outlet tube when the tubes and core are full of water.

Lastly provided is an electronic monitor 82. Such monitor may take the form of a cathode ray tube. Such monitor is coupled to the transducer electronically. In this manner, pressure variations on the central section of the core, as caused by an anal sphincter during orgasm, will cause a change of pressure at the transducer and a resulting electrical pulse or pulses to the monitor to thereby provide a display. Such display exhibits the variation in pressure by the central section of the probe during operation and use.

Figure 4:
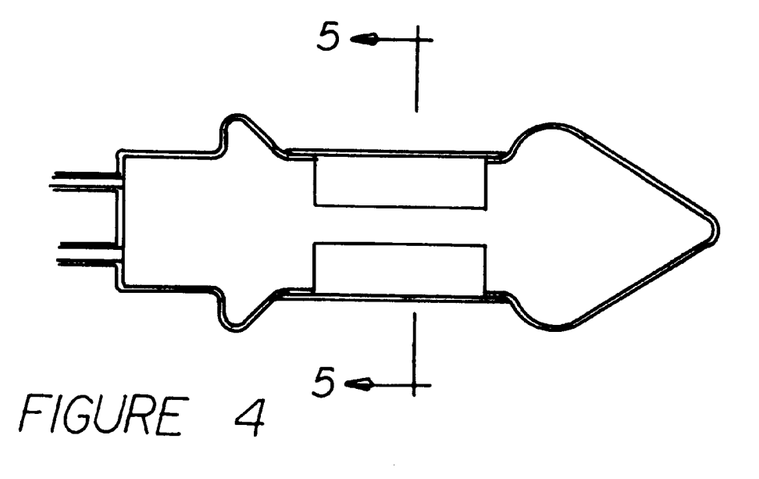
FIG. 4 is a cross-sectional view of a core constructed in accordance with an alternate embodiment of the invention.
Figure 5:
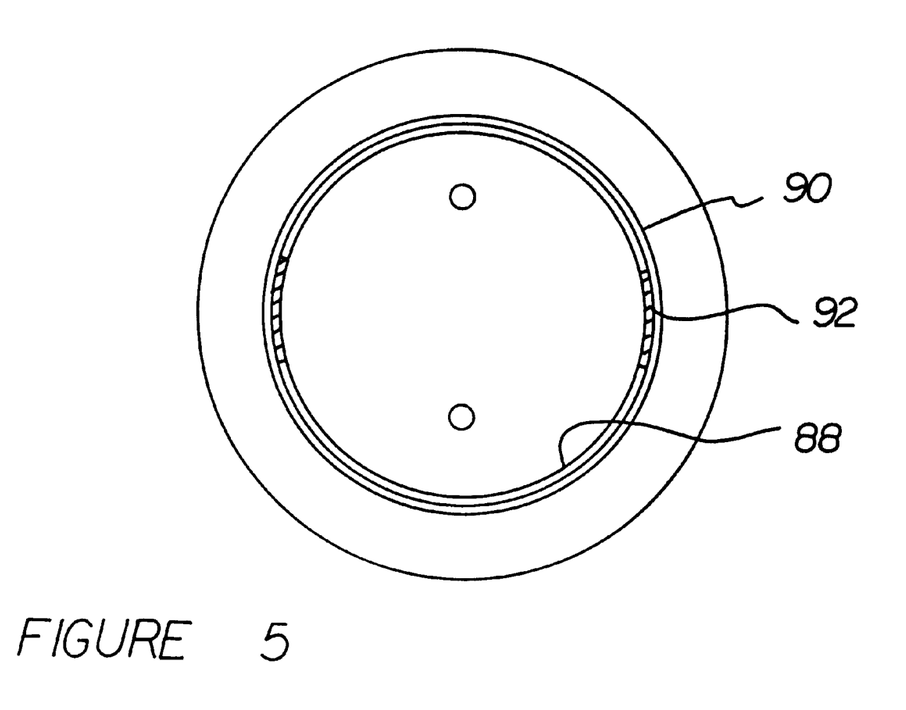
FIG. 5 is a cross-sectional view taken along line 5—5 of FIG. 4.

In an alternate embodiment of the invention as shown in FIGS. 4 and 5, the recess is not utilized. In place thereof, the entire core is filled with water and apertures 88 are formed in the central section of the core. Sheet material 90 constituting windows is in an annular configuration to cover the central section and apertures. An adhesive 92 adheres the sheet material to the core around the apertures.

Figure 6:
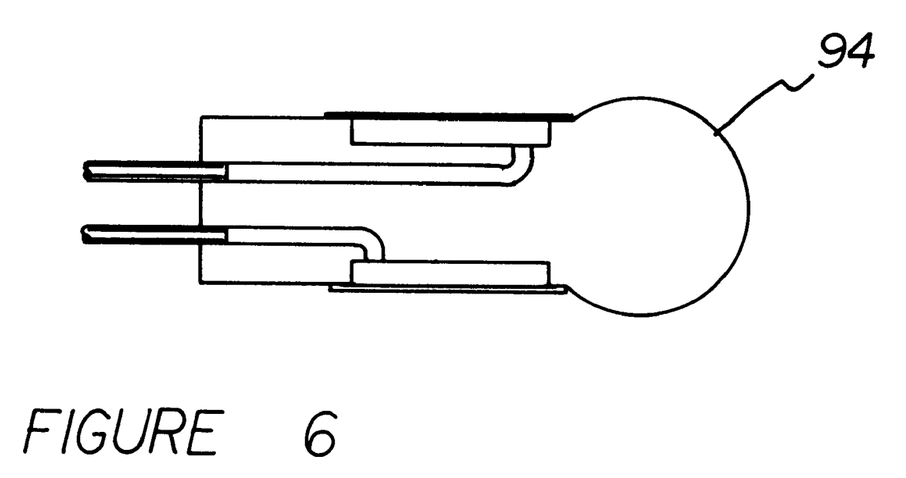
FIG. 6 is an enlarged cross-sectional view of a core constructed in accordance with another alternate embodiment of the invention.
Figure 7:
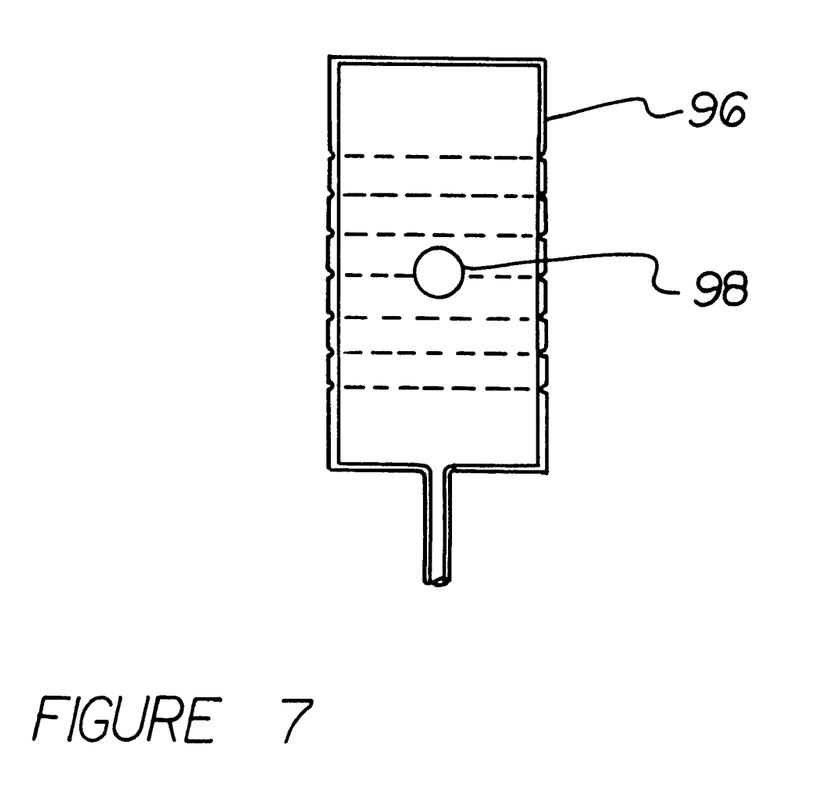
FIG. 7 is a front elevational view of a manometer as used as an alternative to the cathode ray tube of FIG. 1.

FIG. 6 illustrates another alternate embodiment of the invention. In such embodiment no tail is utilized. Further, the head 94 is of an enlarged, generally ball-shaped configuration. Such embodiment is for vaginal use. Lastly, FIG. 7 illustrates an alternate monitor. Such alternate monitor is a manometer 96 with a fluid line at its bottom coupled to the core preferably through the water inlet line. A ball 98 floats on the water line. The ball will thus rise and fall with changes of pressure caused by the core. Indicia lines are preferably formed on the surface of the manometer.

The anal sensor or core of the present invention consists of an enclosed fluid-filled cylinder. It has an insertion or head end, a sensing area or body, and a tail or barrier to limit insertion of the sensor into the anal canal.

The head is conical in shape. The apex of the cone is slightly rounded on its tip to enable the gentle insertion into the anal canal. The base of the cone which is attached to the body has a circumference that is greater than the body of the sensor. The diameter of the base of the cone is approximately ½ inch greater than the diameter of the body. The body or sensing area is approximately 1½ inches long and has a diameter of about ⅞ inch or slightly less. The diameter of the barrier or tail is at least ½ inch greater than the body. Its purpose is to limit further penetration into the anal canal.

The sensor area consists of either an annular recess or two windows running the length of the body symmetrically located on either side of the body and occupying approximately 75 percent of the body surface area in the central section. The body in that central section is then covered with a flexible sheet, preferably a vinyl, making such area a sensing diaphragm.

The anal sensor, and the cylinder, is totally sealed except for two flexible, but relatively rigid, polyvinyl tubes which are inserted through the tail of the sensor and are distal to the barrier. One of the tubes connects the sensor to a transducer. The other is used to fill the sensor, transducer and interconnecting polyvinyl tube with water. It is then sealed, leaving a watertight sensor which is attached to the transducer with rigid and flexible polyethylene tubing.

For insertion into the anal canal, the head is lubricated and gently passed into the anal canal. Once the head passes through the canal, the anal sphincter surrounds the body, the sensing area of the instrument. The enlarged barrier prevents further penetration. This position of the sphincter is maintained by the enlarged head and the barrier which retards further motion. The sensor can be removed at any time by gentle traction on its tail.

The diaphragm or central area of the sensor transmits impulses via the polyvinyl tubing to the transducer. The pulses are then amplified and displayed on a monitoring device. The diaphragm responds to all changes of muscle tone of the anal sphincter and the monitor displays a graphic and quantitative analyses of the sphincter contraction before, during and after orgasm.

In association with the monitoring system as described hereinabove, there is herein provided an alternate embodiment of the invention described hereinafter in three additional embodiments. Such embodiments all relate to a new and useful sexual aid for providing abutment surfaces positionable on opposite sides of an anal sphincter to ensure proper positioning and retention of the sexual aid during use. Such sexual aid may be utilized as a supplement to the system previously described or it may be used by itself.

Figures 8, 11:
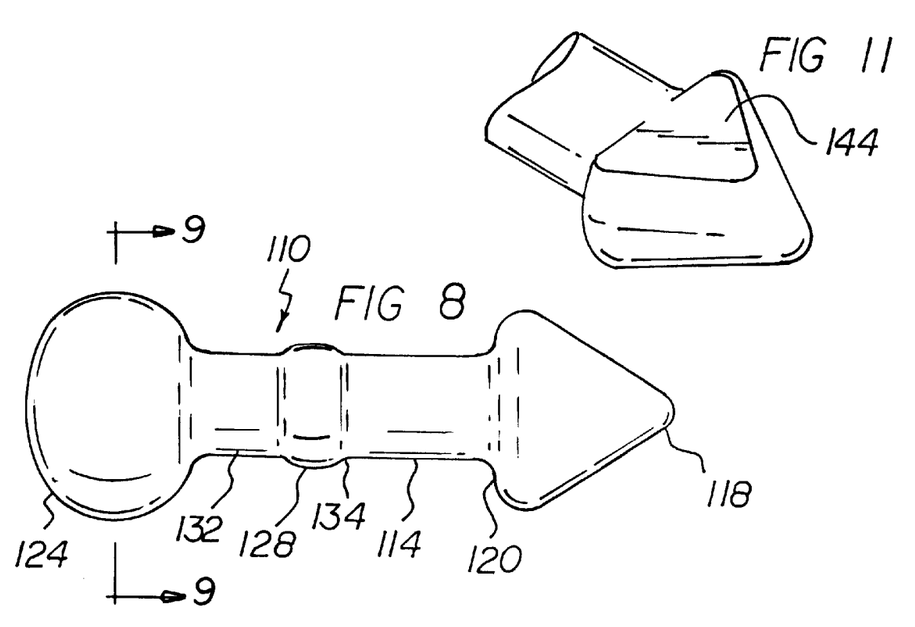
FIG. 8 is a side elevational view illustrating the primary embodiment of the present invention with portions broken away to show certain internal constructions thereof.
FIG. 11 is a perspective illustration of the distal end of the present invention constructed in accordance with another alternate embodiment of the invention.

More specifically, the present invention may be considered as a new and improved sexual aid 10 positionable in a user's anal sphincter for support therein by opposed radial abutment surfaces. A cylindrical central first section 114 has a circular cross-section along its entire length. The central first section has an axial length of about between about 1 inch and 2½ inches, preferably about 1¾ inches and a diameter of between ½ inch and ⅞ inch, preferably ¾ inch.

A distal section 118 is formed in a generally cone-shaped configuration with an axis coextensive with the axis of the central first section. The distal section has a length of between about 1 inch and 2 inches, preferably about 1½ inches and having maximum diameter adjacent to the distal end of the central section with a diameter of between about 1¼ inches and 1¾ inches, preferably 1½ inches to thereby provide a generally planar radial first abutment surface 120 between the central section and the distal section.

Figure 9:
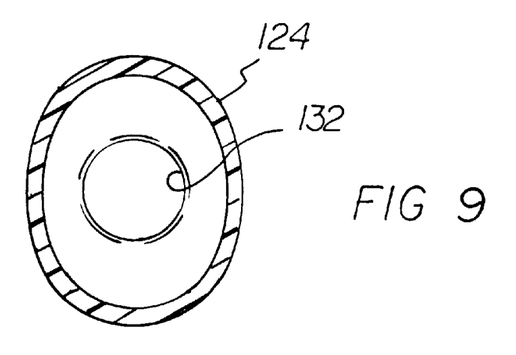
FIG. 9 is a cross-sectional view taken along line 9—9 of FIG. 8.

Next provided is a proximal section 124 in a generally spherical configuration for use as a handle. The proximal section has an axis coextensive with the axis of the central first section and the distal section with a maximum diameter of between about 1½ inches and 2 inches, preferably 1¾ inches;

A central toroidal section 128 is provided between the central first section and the proximal section. The central toroidal section has an axial length of between ¼ inch and ½ inch, preferably ⅜ inches and a maximum radial dimension of between about 1 inches and 1½ inches, preferably about 1¼ inches, providing an enlargement which is between about ½ inch in diameter greater than the cylinders on the opposite sides. A cylindrical second section 132 is provided between the toroidal section and the proximal section. The cylindrical second section has an axial length of between about ½ inch and ¾ inch, preferably ½ inch, and a diameter of between about ½ and ⅞ inch, preferably ¾ inch. The toroidal section forms a second abutment surface 134 between the central first section and the toroidal section. The entire device is formed of an elastomeric material with a lubricous surface and limited resilience.

Figure 10:
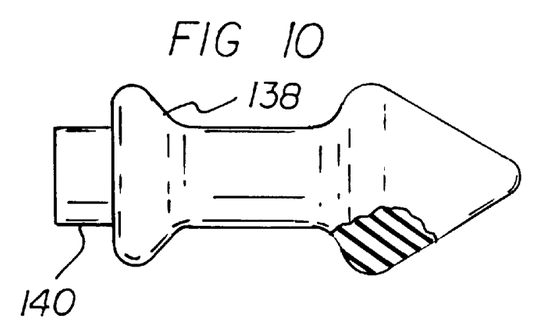
FIG. 10 is a side elevational view of an alternate embodiment of the invention with a portion thereof broken away to show certain internal constructions thereof.

In the embodiment of FIG. 10, the proximal section is generally cone shaped and forms the second abutment surface 138 and further includes a rearwardly extending cylindrical section adapted for use as an additional handle 140.

In the embodiment of FIG. 11, the distal end includes a planar surface 144 extending from the distal tip to the region of the distal end with the greatest diameter and the planar section is adapted for being positioned in the anal sphincter adjacent to the vagina.

In the embodiment of FIG. 10, the entire sexual aid is injection molded of a solid, essentially rigid material with limited resilience from a plastic or rubber or blend thereof preferably polyurethane or a latex.

In the embodiment of FIG. 11, the entire sexual aid is blow molded of a hollow, essentially rigid material with limited resilience from a plastic or rubber or blend thereof preferably polyethylene or a latex.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A new and improved sexual aid positionable in a user's anal sphincter for support therein by opposed radial abutment surfaces comprising, in combination:

a cylindrical central first section, having a circular cross-section along its entire length, the central first section having an axial length of about between one inch and two and one-half inches, preferably about one and three-quarter inches and a diameter of between one-half inch and seven-eighths inch, preferable three-quarter inch;

a distal section formed in a generally cone-shaped configuration with an axis coextensive with the axis of the central first section, the distal section having a length of between about one inch and two inches, preferable about one and one-half inches and having a maximum diameter adjacent to the distal end of the central section with a diameter of between about one and one-quarter inches and one and three-quarter inches, preferable one and one half inches to thereby provide a generally planar radial first abutment surface between the central section and the distal section;

a proximal section in a generally spherical configuration for use as a handle, the proximal section having an axis coextensive with the axis of the central first section and the distal section with a maximum diameter of between about one and one-half inches and two inches preferably one and three-quarter inches;

a central toroidal section between the first section and the proximal section, the central toroidal section having an axial length of between one-quarter inch and one-half inch, preferably three-eighths inch and a maximum radial dimension o between about one inch and one and one-half inches, preferably about one and one-quarter inches providing an enlargement which is between about one-half inch in diameter greater than the cylinders on the opposite sides; and a cylindrical second section between the toroidal section and the proximal section, the cylindrical second section having an axial length of between about two-thirds inch and three-quarter inch, preferably one-half inch, and a diameter of between about one-half and seven-eighths inch, preferably three-quarter inch, and forming a second abutment surface between the central first section and the toroidal section, the entire device being formed of an elastomeric material with a lubricous surface and limited resilience.

2. A sexual aid comprising:

a cylindrical central first section, having a circular cross-section of a first circumference along its entire length;

a distal section formed in a generally cone-shaped configuration with at least a portion of which having a second circumference greater than the first circumference and with an axis coextensive with the axis of the central first section to thereby provide a generally planar radial first abutment surface between the central section and the distal section;

a proximal section for use as a handle, the proximal section having an axis coextensive with the axis of the central first section and the distal section; and a second abutment surface adjacent to the proximal end of the central first section.

3. The apparatus as set forth in claim 2 and further including a central toroidal section between the central first section and the proximal section and a cylindrical second section between the toroidal section and the proximal section.

4. The apparatus as set forth in claim 2 wherein the proximal section is generally cone shaped and forms the second abutment surface and further including a rearwardly extending cylindrical section adapted for use as an additional handle.

5. The apparatus as set forth in claim 2 wherein the distal end includes a planar surface extending from the distal tip to the region of the distal end with the greatest diameter, the planar section adapted for being positioned adjacent to the vagina when the sexual aid is inserted in an anal sphincter.

6. The apparatus as set forth in claim 2 wherein in the entire sexual aid is injection molded of a solid, essentially rigid material with limited resilience from a plastic or rubber or blend thereof.

7. The apparatus as set forth in claim 2 wherein the entire sexual aid is blow molded of a hollow, essentially rigid material with limited resilience from a plastic or rubber or blend thereof.

* * * * *